United States Patent [19]
Illyés et al.

[11] Patent Number: 5,842,975
[45] Date of Patent: Dec. 1, 1998

[54] CONTROLLING AND DATA ACCUMULATING DEVICE ATTACHABLE TO HUMAN BIOLOGIC MEASURING DEVICE

[76] Inventors: Miklós Illyés, H-1182 Budapest, Kótújfalu u. 163; József Vörös, H-1196 Budapest, Hunyadi u. 100; Béla Kövér, H-1086 Budapest, Koszorú u. 18, all of Hungary

[21] Appl. No.: 472,779

[22] Filed: Jun. 7, 1995

[51] Int. Cl.$^6$ ..................................................... A61B 5/00
[52] U.S. Cl. ..................... 600/300; 600/472; 600/500; 439/620; 439/909
[58] Field of Search ................................. 128/672, 677, 128/678, 680, 681, 683, 687, 689; 600/485, 490, 491, 493, 494, 496, 500, 502, 300; 439/620, 909

[56] References Cited

U.S. PATENT DOCUMENTS

| | | | |
|---|---|---|---|
| 4,252,127 | 2/1981 | Gemelke | 128/683 |
| 4,510,942 | 4/1985 | Miyamae et al. | 128/683 |
| 4,562,843 | 1/1986 | Djordjevich et al. | 128/672 |
| 4,830,018 | 5/1989 | Treatch | 128/677 |
| 4,848,361 | 7/1989 | Penney et al. | 128/694 |
| 4,889,132 | 12/1989 | Hutcheson et al. | 128/683 |
| 4,898,180 | 2/1990 | Farrelly et al. | 128/683 |
| 5,002,491 | 3/1991 | Abrahamson et al. | 434/322 |
| 5,178,152 | 1/1993 | Ozawa | 128/680 |

*Primary Examiner*—Jennifer Bahr
*Assistant Examiner*—Bryan K. Yarnell
*Attorney, Agent, or Firm*—Morrison & Foerster LLP

[57] ABSTRACT

Controlling and data accumulating device (1) attachable to a measuring basic apparatus (100) for measuring human biological parameters, preferably blood pressure and/or pulse rate, comprising a measuring unit, sensor (102) data processing microprocessor or microcontroller (101), display (107) and other units. Wherein the microcontroller (2) of the device (1) is connected with the LCD output of the microprocessor (101) of the basic apparatus (100) through an analog demultiplexer (DMP) 10) and comparator (11), furthermore said microcontroller (2) is connected to the control input of the basic microprocessor (101), and the microprocessor (2) of the device (1) is equipped on the one hand with a controlling switch (4) and preferably other handling means connected to different inputs of the microcontroller (2) of the device, and on the other hand with non-volatile memory (7) and a timer (8) with its own power supply (81) as well as through an interface (3) with a special connector (31) to an RS232 line, and preferably with an external power supply.

11 Claims, 2 Drawing Sheets

CONTROLLING AND DATA ACCUMULATING DEVICE ATTACHABLE TO HUMAN BIOLOGIC MEASURING DEVICE

FIELD OF THE INVENTION

The present invention relates to a controlling and data accumulating device attachable to a measuring basic apparatus for human biologic parameters, preferably blood pressure and/or pulse rate, comprising a measuring unit, sensor, data processing microprocessor or microcontroller, display and other units, e.g. power supply unit.

BACKGROUND OF THE INVENTION

Modern medical practice tends to search for and eliminate, or prevent primary causes more and more rather than just cure symptoms. A typical example of this tendency is, that medical needs are not any more satisfied by casual blood pressure measurements, as they are not satisfactorily informative, and enables only symptomatic treatment. The treating physician needs to know the full dynamics of blood pressure trends in connection with usual event of everyday life. Similar needs arise with the observation of other human biologic parameters. Technical development offers solutions in two directions. U.S. Pat. No. 4,803,625 presents a system where patients who need no hospital treatment but continuous home care are observed and taken care of from a central unit in on-line connection. The system is fully electronic and automatic. Contrary to stressed central controlling, the solution presented in EuPat 558 975 is based local controlling, where a flat or an office is fully equipped. Measuring devices, as scales, blood pressure and pulse rate meters, urine analyzers are placed from bathroom through toilette to training room, in armchairs and on beds. A CPU gathers and processes data and gives information on wish on a monitor. Beside such total and very expensive automation, the other direction tends to simplify the patient unit. The applied intelligence is concentrated in a central computer so the patient unit will be simple and inexpensive, but absolutely dependent on the central processing site. Such solution is presented in U.S. Pat. No. 4,830,018, which organizes the software at three levels in-depth data analysis and evaluation is possible at the clinical central unit, examination programs are installed to relatively intelligent units of the area treaters and nurses, while the patient units are only capable of functions necessary for completing due measurements. Eventually, in the prior art there is unknown a fully portable apparatus free from the limitation of on-line system, which is intelligent enough to ensure processable, reliable, structured data masses over an examination period of 1.9 month in order to diagnose health state or set precise dosage and timing of treatment. Such a device would be a novelty in a market gap. A serious obstacle to the production of such a device is that development and (pre)production costs could not be reimbursed, as users with significant purchase potential prefer the above described fully computerized solutions, and the middle class with proper health education and culture who could form a potential market cannot ensure a purchase quantity for an economic production series mass.

SUMMARY OF THE INVENTION

The purpose of the invention is to develop an affordable personal patient unit which can satisfy both medical and patient needs for human biologic parameters measurement is really portable and independent from external power supply. The invention is based on the recognition that the development and produce costs as well as the market-price of the device accordingly the present invention can be significantly reduced developing a controlling and data accumulation device attachable to existing human biologic parameter measuring apparatus which are modern and reliable but which miss the necessary intelligence and the resulting scale of functions.

We arrived at the recognition basing the present invention that we can decode four level double multiplexed display driver signals with one comparator and demultiplexer, so the controlling and data accumulating device can easily be attached to any existing human biologic parameter measuring apparatus.

We also arrived at the recognition leading to the invention that the I/O bus (in our example an RS232 line) connector and the net adaptor connector of the in-built batteries can be combined, providing the operation of this combined connector is controlled by the transferred signal level itself.

Finally we arrived at the recognition leading to the invention that the direct connection created between the in-built timer unit and the power supply voltage stabilizer can reduce the power consumption of the portable device by a magnitude, so its weight and size can be those of a comfortable personal device.

Accordingly, the invention relates to a controlling and data accumulating device attachable to a measuring basic apparatus for human biologic parameters, preferably blood pressure and/or pulse rate, comprising a measuring unit, sensor, data processing microprocessor or microcontroller, display and other unit, e.g. power supply unit, wherein one of the output of the microcontroller of the said device is connected to the controlling input of the measuring microcontroller of the basic apparatus, another output to an analog demultiplexer/DMP/, the output of the said DMP to one input of a comparator, and the said comparator's output to the input of the microcontroller of the said device; and this said microcontroller is equipped on the one hand with a controlling switch and preferably other handling possibilities, connected to different inputs of the said microcontroller, and on the other hand with non-volatile memory and a timer with an own power supply, as well as it is connectable through a special connector to an RS232 line or an external power supply.

With a preferred embodiment of the above mentioned device the RS232 line connector and the external power supply connector are united in a combined connector.

The device accordingly the present invention preferably for handling it is equipped with an event marker switch, which serves the purpose of storing the actual time (date, hour, minute) of switching accompanied by a marker flag readable by an external device.

With an other preferred embodiment the microcontroller of the device is equipped with a multi position level switch for handling, to the positions of which discrete controlling value levels, e.g. maximum pressure values (blood pressure measuring unit inflation pressure end limit) can be ordered. The said device preferably is equipped with a signal unit connected to the microcontroller (beep/buzzer). With a further preferred embodiment the said timer unit is in direct connection with a power supply and/or (voltage stabilizer unit either previously built in the attached apparatus or placed in the device which direct controlling connection enables the timer unit to switch the attached apparatus on and place it under voltage in its off state. The said preferred embodiment supplied with multi-position level switch wherein at least one position of the multi-position level switch is in direct hardware connection with an area of the microcontroller, which, based on the gathered measurement data, can set an actual inflation pressure end limit value and order this value to the said position of the switch.

The invention will be described in detail by means of a preferred embodiment, with reference to the drawings enclosed, not limiting however either the application range of the present invention or our claims to the presented examples.

BRIEF DESCRIPTION OF THE PREFERRED EMBODIMENT

Figure 1:
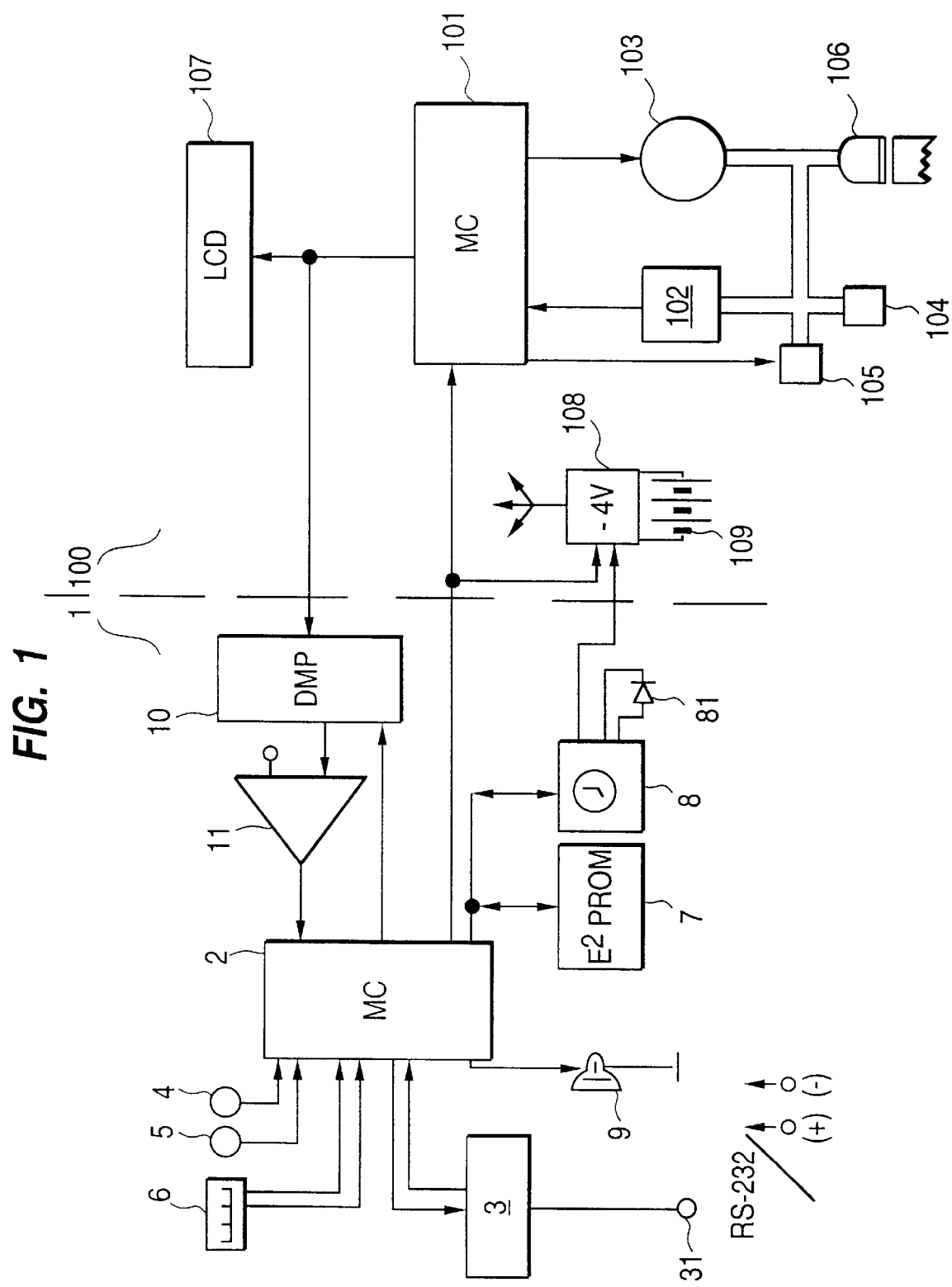
FIG. 1. The block schematics of the invented device attached to a measuring apparatus FIG. 2. The circuit diagram of the combined connector

FIG. 1. shows the invented controlling and data accumulating device 1 attached to a blood pressure measuring basic apparatus 100. The measuring unit connector 106 of the said apparatus 100 connects the apparatus to its measuring unit /not shown/ The measuring unit in this case is an inflatable cuff to be placed on the patient's arm. Double lines without arrowheads in the FIG. 1. represent pneumatic connections. The measuring unit connector 106 is in pneumatic connection with a motor pump 103, a sensor 102, in this case a capacitive pressure sensor, a pressure dropper 105 and a pressure deflator 104. The pressure deflator 104 is a slow release valve with measured opening while the pressure dropper 105 is a quick release valve controlled by the measuring microcontroller 101 of the apparatus. The output of the sensor 102 is connected to the signal input of the measuring microcontroller 101, one controlling output of the said microcontroller is connected to the motor pump 103, another controlling output to the pressure dropper 105. The measuring microcontroller 101 receives control on its controlling inputs, and it transfers the output signals with double multiplexed four voltage level LCD driving to the display 102 attached to it, in this case a liquid crystal display LCD. The apparatus 100 is well declared and known in itself.

The controlling outputs of the microcontroller 2 of the invented device 1 are connected to the controlling inputs of the measuring microcontroller 101 of the basic apparatus 100. The microcontroller 2 may be an appropriate, existing, programmable microelectronic component e.g. PIC 16C57 or other similar equivalent product. A further output of the microcontroller 2 is connected to the MC input of the analog demultiplexer (DMP) 10 while the LCD inputs of the demultiplexer 10 are connected to wires coming from the outputs of the LCD 107. The output of the demultiplexer 10 is connected to the input of the comparator 11, the output of the comparator 11 is connected to the microcontroller 2. The controlling output of the microcontroller 2 is connected to the stabilizer 108 giving a stabilized voltage of −4V, which receives power supply from the battery 109 or a net adaptor through the external power supply connector 31. All components of the apparatus 100 and the device 1 receive power supply through the appropriate points from stabilizer 108. These points are not shown in FIG. 1 for simplicity reasons; we only sign power output at the stabilizer 108 with a triple-arrowhead line. The microcontroller 2 is connected through an $E^2C$ bus to the memory 7, which is non-volatile RAM ($E^2$PROM); and to the timer unit 8 with its own power supply 81; and further through another controlling input to a signal unit 9, in this case a piezo beeper. The timer unit 8 has a direct awakening connection through a separate wire to the stabilizer 108.

For control of the microcontroller 2 serve connected to its controlling output the pushbutton controlling switch 4, event marker switch 5, and the four-position level switch 6. Connection to an external computer or to external power supply (net adaptor) is made possible by the connector 31 connected to the microcontroller 2 through an RS232 level linking interface 3.

Figure 2:
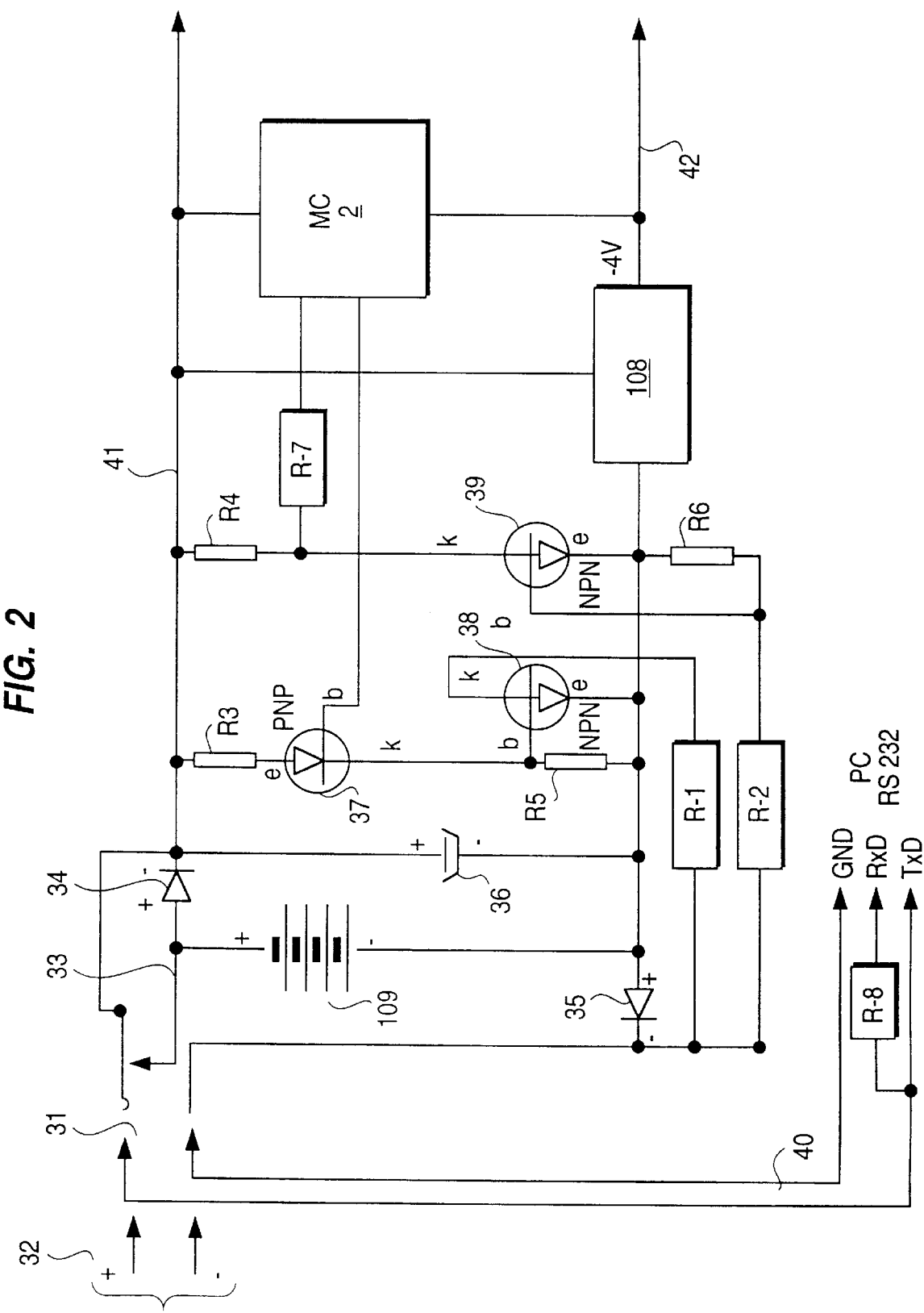

The programs burnt into the microcontroller 2 of the invented device 1 will be described in detail in the section on operation and application of the device 1. The combined connector 31 can be realized by the application of circuitry comprising three transistors, two diodes, and a switch 33 as shown in FIG. 2. Thus the connector 31 is capable of receiving either an RS232 cable 40 or a net adaptor 32. The positive input point of the connector 31 is the switch 33, one end of which is connected to the positive pole of the batter 109 and to the anode of the positive branch diode 34, while the other end is connected to the cathode of the positive branch diode 25 as well as to the positive pole of the capacitor 36. The negative input point of the connector 31 is connected to the cathode of the negative branch diode 33, and through resistor R1 to the collector of the NPN primary transistor 38, as well as through resistor R2 to the basis of the NPN stabilizer transistor 39. The anode of the negative branch diode 35 is connected to the positive poles of the battery 109 and the capacitor 36, as well as through the resistor R4 to the basis of the NPN primary transistor 38 and to the collector of the PNP transistor 37, while directly to the emitters of the primary transistor 38 and the stabilizer transistor 39 and to the negative input of the stabilizer 108. To the positive branch 41 coming from the cathode of the positive branch diode 34 is connected through the resistor R3 the emitter of the PNP transistor 37, through the resistor R4 the collector of the stabilizer NPN transistor 39 (the latter being in connection through the resistor R7 with the microcontroller 2 as well), and directly the stabilizer 108 and the microcontroller 2. The microcontroller 2 is on the other hand connected to the −4V voltage level negative branch of the stabilizer 108. Connecting the net adaptor 32, its positive output is connected to the switch 33 of the connector 31, and its negative output to the negative input of the connector 31. An external computer (PC) can be connected through an RS232 line 40 to the connector whereas the PC ground point is connected to the negative input of the connector 31, while RxD point directly and TxD point through a resistor R8 to the switch 33 of the connector 31.

The measuring apparatus 100, in this case a blood pressure monitor, operates without the attachment of the invented device 1 as follows: for a starting signal from the handling switches, in lack of the device 1 connected directly to the measuring microcontroller 101 of the basic apparatus 100, and for the resulting controlling signal from the measuring microcontroller 101, the motor pump 103 transports air through the measuring unit connector 106 to the measuring unit, thus increasing the pressure inside, about which, converted to electric signals, the sensor 102 brings information to the measuring microcontroller 101. The latter, when the pressure in the measuring unit reaches a level preset in its in-built program, stops the motor pump 103, pressure is slowly decreased through the pressure deflator 104. The continuously measured pressure values are processed according to the in-built program by the measuring microcontroller 101, and the results are transferred with double multiplexed four voltage level LCD driving to the display 107.

With the attachment of the invented device 1, the first signal from the controlling switch 4 is interpreted by the microcontroller 2 as on/start signal, and it awakens and starts the measuring microcontroller 101. When the measurement process is completed, signal from the same switch is interpreted as off. With the measurement process running, the signal of this switch is interpreted by the microcontroller 2 as the interrupt, so the process is interrupted, and the pressure dropper 105 is opened, resulting in an instant quick pressure release. It is necessary if the examined person experiences pain arising from the pressure on his arm applied by the measuring unit, or has any other reason to interrupt the measurement process. As a result of the signal from the event marker switch 5, the microcontroller 2 calls the actual time from the timer unit 8, and transfers it with an appropriate flag to the memory 7 for storing, simultaneously giving an acoustic signal of acknowledgement through the signal unit 9.

With the controlling switch 4 held pressed down, the event marker switch 5 will cause an operation mode change. Operation modes are the following 1. The invented device works in manual mode, i.e., a measurement is initiated on manual start signal, the result is processed and stored together with the proper date and time.

2. The invented devices works in semi-automatic mode, i.e., it gives an acoustic signal through the signal unit 9 each time a measurement is due, or e.g. a medicine should be taken according to a stored medical schedule.

3. The invented device works in automatic mode, starting measurements according to a stored medical schedule automatically.

In all three modes, processing, displaying and storing the data happens automatically.

The four positions of the multi-position level switch 6 are ordered to a certain pressure value. The user of the apparatus 100 can select the value reaching which the motor pump 103 stops functioning. This function is the same as in the original measuring apparatus 100.

Through the interface 3 the microcontroller 2 can be connected to an external computer (PC) which has an RS232 input. Through this channel, data and stored events can be loaded to the external computer for complex diagnostic evaluation, and from the external computer the medical schedule can be loaded to the invented device, worked out by the physician for the examined person regarding the order of measurements to be taken.

The measurement results are transferred from the measuring apparatus 100 to the invented device 1 as follows: With the help of the demultiplexer 10 and the comparator 11 the signal combinations to toward the display 107 are decoded, namely, by creating as many LCD inputs on the demultiplexer 10 as has the display 107. Signal combinations transferred toward the display 107 inputs are also received by the LDC inputs of the demultiplexer 10. The microcontroller 2 controls the demultiplexer 10 through a five channel connection: it addresses its LCD inputs in order, and asks them in order according to addressing, interpreting the received signals with a decoding program as digital data in the microcontroller 2, handling and storing those in the memory 7.

The combination connector 31 as shown in FIG. 2. works as follows:

On connecting the adaptor 32 the switch 33 is open, the positive branch diode 34 closes from the direction of the positive branch 41, and the negative branch diode 35 is open in the direction of the negative input of the connector 31. On connecting the RS232 cable 40, on data transfer from the PC to the device 1, the primary transistor 38 closes, and at −12V voltage level arriving from the TxD point the negative branch diode 34 acts as open, and due to the resistors R2 and R6 acting as voltage divider, the stabilizer transistor 39 closes. At a −12V voltage level of the TxD, a 18V voltage appears on the negative branch diode 35 and it acts as closing unit, but due to its effect, the stabilizer transistor 39 opens. When the PC does not act as transmitter, on the cathode of the negative branch diode a voltage of 18V appears, and −6V on the RxD cable line. On data transfer from the device 1 to the PC, the primary transistor 38 opens and a voltage of −6V appears on the RxD line.

The separate controlling connection between the timer unit 8 and the stabilizer 108 helps achieve better power management. To achieve this, after finishing the measurement process the microcontroller 2 switches the apparatus 100 and the device 1 off, including itself, but previously programs the timer unit 8 to switch the system on at a defined time. The timer unit 8 receives power from its own supply unit 8, but can only awake the system if it has direct connection to the stabilizer 108, so it can awake the stabilizer 108 at the defined time, thus ensuring power supply for the microcontroller 2, capable of restarting the whole device 1.

The multi-position level switch 6 is a component of the measuring apparatus 100, and it enables selection among four preset inflation pressure end limits. With the attachment of the invented device 1, at least one position of this switch 6 is in hardware connection with a sector of the microcontroller 2, which generates a new inflation pressure end limit for this position of the switch 6 automatically, based on processing of previously measured values.

The invention is a controlling and data gathering device which is adaptable to any measuring device with a microprocessor of microcontroller that uses electronic signal sequences as data output. The invented device is capable of decoding of double multiplexed four voltage level signals very simply with the help of an analog demultiplexor and a comparator, enabling the handling, processing and storing of these signals by a microcontroller.

In the case of the example, namely the blood pressure monitor, this enables that the examined person be under close observation with data storage for several months, so the effect/dosage of applied medicines can be judged/set based on a significant number of measurements and a representative time period. There is no need to examine the person in medical environment three times a day. This is not only cost-and effort-saving, but also enhances the reliability of the measurement data, as the professionally well-known disadvantageous distorting "white-coat effect", i.e., the distortion of blood pressure values due to the medical stress situation can be eliminated.

When processing the data, data and time references are also available, without which one cannot really judge the medicine effect. The device warns the examined person to take the medicine (and to measure in semi-automatic mode). Warning acoustic signals are generated due to a medical schedule worked out by the physician and loaded to the device from the physician's computer.

Summarized, the invention made it possible to create an additional device ensuring numerous new functions on the user side, which not only automates the basic measuring apparatus, but also enables the solution of several formerly unsolved problems. The invention gives this to the user with a low cost, simple component structure, ensuring simple operation.

We claim:

1. A control and data accumulating device attachable to a measuring apparatus for measuring basic biologic parameters including at least one of blood pressure and pulse rate, the measuring apparatus having a measuring unit, a sensor, a data processing microprocessor, and a display unit, said control and data accumulating device comprising:

a microcontroller coupled to a control input of the measuring apparatus, said microcontroller selectively sending control signals including a start signal and a stop signal to the measuring apparatus;

a demultiplexer coupled to an input side of the display unit of the measuring apparatus, said demultiplexer receiving display data sent to the display unit by the measuring apparatus;

a comparator, coupled to said demultiplexer and to said microcontroller, for conveying the display data from said demultiplexer to said microcontroller such that the display data arrives at the microcontroller at substantially a same time as the display data arrives at the display unit;

a connector having circuitry which enables the connector to alternately connect to an external power supply and an external computer through a communication cable.

2. The control and data accumulating device of claim 1, wherein said microcontroller has a plurality of inputs, and wherein at least one of following is connected to an input of said microcontroller: (i) a controlling switch; (ii) a peripheral device; (iii) a non-volatile memory; (iv) a timer; and (v) an interface unit for linking said control and data accumulating device to an external device.

3. The control and data accumulating device of claim 2, wherein the external device comprises an external power supply or an external computer.

4. The control and data accumulating device of claim 3, wherein said interface unit comprises a RS232 connector and a net adaptor united into one combined connector.

5. The control and data accumulating device of claim 2, wherein said interface unit comprises a RS232 connector and a net adaptor united into one combined connector.

6. The control and data accumulating device of claim 2, wherein said peripheral device comprises an event marker switch.

7. The control and data accumulating device of claim 2, wherein said peripheral device comprises a level switch having multiple positions.

8. The control and data accumulating device of claim 7, wherein at least one position of said level switch is in direct hardware connection with an operative part of said microcontroller.

9. The control and data accumulating device of claim 2, wherein said peripheral device comprises an acoustic signal unit.

10. The control and data accumulating device of claim 2, wherein said timer is coupled to at least one of a built-in power supply and a stabilizer of the measuring apparatus, said timer controlling the at least one of the built-in power supply and the stabilizer using a predefined timing.

11. A control and data accumulating device attached to a measuring apparatus for measuring biologic parameters, the measuring apparatus having a measuring unit, a sensor, and a display unit, said control and data accumulating device comprising:

a non-volatile memory accumulating the data received from the measuring apparatus; and a connector having circuitry which enables the connector to alternately connect to an external power supply and an external computer through a communication cable.

* * * * *